United States Patent [19]
Fujimori et al.

[11] Patent Number: 5,801,202
[45] Date of Patent: Sep. 1, 1998

[54] AMINE DERIVATIVES FOR TREATMENT OF SKIN DISORDERS

[75] Inventors: Taketoshi Fujimori; Hiroshi Kusuoku, both of Ichikai-machi; Akira Yamamuro, Utsunomiya; Yukihiro Yada, Ninomiya-machi; Kazuhiko Higuchi, Utsunomiya; Genji Imokawa, Utsunomiya; Naoki Kondo, Utsunomiya; Yoshinori Masukawa, Utsunomiya; Hajime Tokuda, Utsunomiya; Hisashi Tsujimura, Ichikai-machi, all of Japan

[73] Assignee: Kao Coproration, Tokyo, Japan

[21] Appl. No.: 817,928

[22] PCT Filed: Nov. 8, 1995

[86] PCT No.: PCT/JP95/02284

§ 371 Date: May 30, 1997

§ 102(e) Date: May 30, 1997

[87] PCT Pub. No.: WO96/15098

PCT Pub. Date: May 23, 1996

[30] Foreign Application Priority Data

Nov. 9, 1994 [JP] Japan ........................ 6-274874
Nov. 9, 1994 [JP] Japan ........................ 6-274875

[51] Int. Cl.$^6$ ........................................ A01K 31/13
[52] U.S. Cl. ........................ 514/659; 564/507; 564/487; 564/445; 564/453; 564/462; 564/504; 514/668; 514/669; 549/551
[58] Field of Search ........................ 564/507, 487, 564/445, 453, 462, 504; 514/659, 668, 669; 549/551

*Primary Examiner*—Brian M. Burn
*Attorney, Agent, or Firm*—Oblon, Spivak, McClelland, Maier & Neustadt, P.C.

[57] ABSTRACT

Disclosed is an amine derivative represented by the following formula (1) or an acid addition salt thereof:

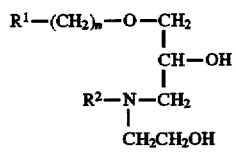

wherein $R^1$ represents a group

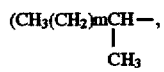

a cyclopentyl group, cyclohexyl group, or a cycloheptyl group, $R^2$ is a hydrogen atom or C1–C3 alkyl group which may be substituted by one or more hydroxyl groups, m is an integer falling in the range from 3 to 5 inclusive, and n is an integer falling in the range from 9 to 11 inclusive. Also, intermediates useful in the manufacture of the amine derivative (1), compositions for external application to the skin containing the amine derivative, and keratinization improvers containing the amine derivative as an active component are described. The compound (1) has excellent keratinization improving action, pigmentation preventing action, etc.

12 Claims, 3 Drawing Sheets

AMINE DERIVATIVES FOR TREATMENT OF SKIN DISORDERS

This application is a 35 USC 371 of PCT/JP95/02284, filed Nov. 8, 1995.

TECHNICAL FIELD

The present invention relates to novel amine derivatives, acid addition salts thereof, and novel glycidyl ether derivatives which are intermediates in the process of preparing the amine derivatives and acid addition salts. The compounds encompassed by the present invention dramatically improve keratinization, prevent or improve pigmentation of skin, and solve skin problems caused by dyskeratosis.

DESCRIPTION OF THE RELATED ART

The outermost layer of the skin called the epidermis prevents water loss and loss of a variety of components from living bodies and controls the homeostasis of living bodies. Moreover, the epidermis functions as a barrier and protects the body from outside physical and chemical stimulation (heat, humidity, etc.) and also from various bacteria. Thus, its physiological functions are very important for the activities of living bodies. Keratinocytes, which constitute the epidermis, form healthy epidermis having the above-mentioned physiological functions when cell proliferation and keratinization (differentiation) are well balanced. However, if this balance is lost due to the presence of intra- or extra- corporeal factors that affect living bodies including excessive stimulation (for example, UV-rays) from the environment and degradation of physiological functions (for example, aging of skin accompanying senility, diseases, etc.), healthy epidermination cannot occur. Particularly, the face and hands which are usually exposed to stimulation by UV rays, etc. are generally in a condition where proliferation is excessive and keratinization is insufficient. This induces acanthosis and parakeratosis, and as a result, ordinary skin complaints such as dry skin, fatty skin, and dandruff are caused. Furthermore, formation of keratinous plugs is considered to cause various troubles in the skin including generation of acne, and delay in melanin metabolism to cause pigmentation of skin.

Approaches to restore such abnormal skin conditions and to keep the skin healthy include removal or suppression of causal substances or conditions and addition or application of a certain components. Previously, a primary care for preventing and solving skin problems employed synthetic or natural moisture-retainable components which prevent the skin from drying and enhance the moisture-retention ability of the skin, thereby compensating the decrease in moisture-retaining ability of the skin. Alternatively, circulation promoters were applied to the skin to accelerate blood circulation in the skin. Moreover, spots, freckles, and pigmentation caused by sunburns and suntans tend to easily occur or increase in number as the skin ages, and in addition, they do not disappear easily, so they are a source of complaints to middle aged to elderly persons. The onset mechanism of these pigmentations of the skin has not yet been elucidated. However, it is considered that sunlight, particularly UV rays, and melanocyte stimulating hormones act to stimulate the melanin-synthesizing mechanism in epidermal melanocytes. Conventionally, in order to blanch acquired pigmentation of melanin described above to a normal skin color, vitamin C (ascorbic acid) derivatives and isoflavon derivatives (Japanese Patent Application Laid-open (kokai) No. 58-225004) have been used as well as p-hydroxycinnamic acid derivatives (Japanese Patent Application Laid-open (kokai) No. 59-196813).

However, the above-mentioned conventional approaches have various problems with respect to the ability of preventing skin problems, efficacy in improvement, sustainability of the effect, and stability/safety of the composition. That is, since the conventional methods are intended to supply water or to supplement part of moisture-retaining components to the epidermis, particularly the surface of the horny layer, they produce only temporary effects, and accordingly, long-lasting and radical alleviation of skin problems were not expected. Moreover, as regards the pigmentation, substances having excellent effects of preventing and relieving of pigmentation have not yet been found.

Accordingly, there is still a hope for the development of a substance which satisfactorily suppresses parakeratosis, acanthosis, and metabolic error of lipids, which excellently prevents and improves pigmentation of the skin to retard aging of the skin, and which remarkably ameliorates skin problems caused by dyskeratosis.

Under the above circumstances, the present inventors previously carried out extensive studies, and found that certain amine derivatives are effective in retarding aging of the skin by normalizing keratinization and preventing and ameliorating pigmentation of the skin. They filed patent applications (Japanese Patent Application Laid-open (kokai) Nos. 5-194185 and 6-271450) directed to the above finding. Among the compounds disclosed in the specifications of these patent applications, the compounds represented by the following formula (A) have particularly excellent effects in retarding aging of the skin by normalizing keratinization and preventing and ameliorating pigmentation of the skin.

(A)

wherein a and b are numbers which satisfy the conditions of a+b=11 to 17, a=4 to 10, b=5 to 11, and having a distribution with an apex at a=7 and b=8.

The above amine derivatives (A) are obtained using isostearyl alcohol as a starting material, which is prepared by reducing isostearic acid, a by-product in the manufacture of dimer acids from beef tallow, soybean oil, etc. Therefore, they are mixtures of compounds having methyl branches at a variety of positions on the principal chain. The present inventors, noting that these compounds have excellent effects in normalizing keratinization and preventing and ameliorating pigmentation of the skin though they are mixtures, started to search for the active components of the amine derivatives (A) in the form of a mixture. They conducted fractionation by HPLC and structure determination by GC-MS, and found that the compound group having the following formula (B) have excellent effects in normalizing keratinization.

(B)

wherein $R^b$ is an alkyl group having a total of 17 carbon atoms and having a single methyl group at one of 7- to 15-positions.

The compounds (B) are contained only in amounts of about 3% in the aforementioned amine derivatives (A).

The present inventors synthesized and evaluated the compounds (B) one by one, and also searched for diverse analogous compounds. As a result, they found that the amine derivatives of the following formula (1) normalize keratinization, prevent and ameliorate pigmentation of the skin, and solve skin problems caused by dyskeratosis to a degree much greater than the above-mentioned amine derivatives (A). The present invention was accomplished based on this finding.

DISCLOSURE OF THE INVENTION

The present invention provides an amine derivative represented by the following formula (1) or an acid addition salt thereof:

wherein $R^1$ represents a group a cyclopentyl group, cyclohexyl group, or a cycloheptyl group, $R^2$ is a hydrogen atom or C1–C3 alkyl group which may be substituted by one or more hydroxy groups, m is an integer falling in the range from 3 to 5 inclusive, and n is an integer falling in the range from 9 to 11 inclusive.

In a preferred emdodiment of the present invention $R^1$ represents a and the sum of m and n is 14 and/or $R^2$ represents a hydrogen atom.

The present invention also provides a glycidyl ether derivative which is useful as an intermediate in the manufacture of the amine derivatives (1). The glycidyl ether derivative is represented by the following formula (2):

wherein $R^1$ represents a group a cyclopentyl group, cyclohexyl group, or a cycloheptyl group, m is an integer falling in the range from 3 to 5 inclusive, and n is an integer falling in the range from 9 to 11 inclusive.

The present invention moreover provides a topical composition comprising the above-mentioned amine derivative (1) or an acid addition salt thereof.

The present invention also provides use of the above-mentioned amine derivative (1) or an acid addition salt thereof as a topical composition for external application to skin.

In a further aspect the present invention relates to the use of the amine derivatives with formula (1) or their acid addition salts for the manufacture of topical compositions for treating dyskeratosis and related diseases, acanthosis and comedo as well as for improving the keratinization and pigmentation of the skin.

The present invention further provides a keratinization improver comprising, as an active component, the above-mentioned amine derivative (1) or an acid addition salt thereof.

The present invention further provides a method for improving keratinization by applying an effective amount of the above-mentioned amine derivative (1) or an acid addition salt thereof to the human skin.

BEST MODE FOR CARRYING OUT THE INVENTION

In formula (1) which represents the amine derivative (1) of the present invention, specific examples of $R^1$ include 1-methylpentyl, 1-methylhexyl, 1-methylheptyl, cyclopentyl, cyclohexyl, and cycloheptyl. Particularly, 1-methylpentyl, 1-methylhexyl, 1-methylheptyl, and cyclohexyl are preferred.

Examples of $R^2$ include a hydrogen atom, C1–C3 alkyl groups, and C1–C3 hydroxyalkyl groups. Preferred ones are hydrogen, methyl, ethyl, n-propyl, and 2-hydroxyethyl, with hydrogen, methyl, and 2-hydroxyethyl being particularly preferred.

As examples of the acid addition salt of the amine derivative (1) of the present invention, there are inorganic acid salts such as hydrochlorides, nitrates, sulfates, and phosphates and organic acid salts such as succinates, fumarates, hexadecanoates, octadecanoates, lactates, glycollates, citrates, tartarates, and benzoates.

Since the amine derivative (1) contains an asymmetric carbon atom, the compounds of the present invention may have stereoisomers. Such stereoisomers and mixtures of the stereoisomers are also in the scope of the present invention. Moreover, the compounds of the present invention may be present as solvates such as hydrates.

The amine derivatives of the present invention represented by formula (1) can be prepared by various methods. For example, they can be prepared by first reacting alcohol (3) with epichlorohydrin in the presence of a base and a phase-transfer catalyst to form a glycidyl ether derivative (2), and then reacting the glycidyl ether derivative (2) with an amine (4) as shown by Reaction Scheme (a) below.

wherein $R^1$, $R^2$, and n have the same meaning as defined before.

Among the alcohols (3) which can be used as the starting material, those in which $R^1$ is can be prepared by a Grignard reaction shown by Reaction Scheme (b) below using a alcohol halide (5) and a ketone (7).

wherein m and n have the same meaning as defined before.

Moreover, among the alcohols (3) which can be used as the starting material, those in which $R^1$ is cyclopentyl, cyclohexyl, or cycloheptyl can be prepared in a manner similar to Reaction Scheme (b) except that cyclopentanone, cyclohexanone, or cycloheptanone are used in place of ketone (7).

Non-limiting examples of the base used in Reaction Scheme (a) include sodium hydroxide, and those of the phase-transfer catalyst include n-tetrabutylammonium bromide.

The reaction between alcohol (3) and epichlorohydrin may be carried out as follows. First, 1–4 mols of epichlorohydrin and 0.01–0.05 mols of a phase-transfer catalyst are added to 1 mol of alcohol (3). While stirring at a temperature of 20°–100° C., 1–4 mols of a base is added to the resulting mixture, followed by stirring for several hours at 20°–100° C. In this reaction, solvents are not necessarily needed. However, any solvent can be used as long as it is inactive in the reaction. For example, n-hexane, 1,4-dioxane, toluene, benzene, and tetrahydrofuran may be suitably used.

As examples of suitable amines (4), mention may be given to ethanolamine, N-methylethanolamine, and diethanolamine.

The reaction between a glycidyl ether derivative (2) and an amine (4) may be carried out by adding 0.5 to several hundreds mols of an amine (4) to 1 mol of a glycidyl ether derivative (2), and stirring for several hours at 20°–100° C.

In this reaction, solvents may not usually be present. However, any solvent can be used as long as it is inactive in the reaction. For example, methanol, ethanol, isopropyl alcohol, tetrahydrofuran, and 1,4-dioxane may be suitably used.

The amine derivative (1) thus obtained can be, if desired, converted into the aforementioned inorganic or organic salts by known methods.

As described in Examples hereinafter, the amine derivatives (1) remarkably promote differentiation of epidermal cells, suppress acanthosis, and prevent or improve pigmentation of the skin even at such a low concentration that compounds (A) disclosed in the aforementioned previous applications, i.e., Japanese Patent Application Laid-open (kokai) No. 5-94185 or 6-271450 cannot exhibit satisfactory effects. More specifically, the compounds (1) of the present invention have higher effects than the compounds, including compounds (A), disclosed in those two prior art publications in terms of retardation of aging of the skin by improving keratinization and preventing and improving pigmentation of the skin. Moreover, the amine derivatives (1) were found to inhibit formation of comedos, which effect was not obtained by compounds (A) of the previous applications. From this, it is understood that the amine derivatives (1) are effective in relieving a variety of skin problems such as acne and dandruff which are considered to be attributed to dyskeratosis in addition to the above-described effects in suppressing acanthosis causable by UV rays and preventing the skin from aging, i.e., preventing and improving pigmentation of the skin.

The amine derivatives (1) of the present invention are incorporated in topical compositions, i.e. compositions for external application to the skin. The compositions may be formulated toward diverse applications. For example, the amine derivatives (1) may be formulated into medicated compositions for external use, skin-care compositions for external use, and cosmetic compositions.

Examples of medicated compositions for external use and skin-care compositions for external use include, for example, various ointments containing medicinal ingredients.

The base of the ointments may be either an oil or an emulsion (oil-in-water or water-in-oil). Oily bases which can be used are not particularly limited, and mention may be given to vegetable oils, animal oils, synthetic fatty acids, and natural or synthetic glycerides. Also, medicinal ingredients are not particularly limited. For example, analgesic/antiphlogistic agents, analgesic agents, bactericidal/disinfecting agents, astringents, skin ointments, hormones, and vitamins may be used as needed.

If the amine derivatives (1) are intended to be formulated into cosmetic compositions, they are combined with a suitable combination of oils, humectants, UV absorbers, alcohols, chelating agents, pH adjusters, preservatives, thickeners, colorants, perfumes, vegetable extracts, etc. which are commonly used as cosmetic ingredients.

As examples of cosmetic compositions to which the compounds of the present invention may be applied, there are water-in-oil or oil-in-water emulsion cosmetic compositions, creams, milky lotions, toilet waters, oily cosmetic compositions, lipsticks, foundations, skin detergents, hair tonics, hair styling agents, hair growing agents, and hair nourishing agents.

The amount of amine derivatives (1) incorporated into compositions for external application to the skin is not particularly limited. However, it is preferred that the amine derivatives (1) be incorporated in amounts from 0.005 to 10% by weight (hereinafter simply referred to as %), and particularly from 0.05 to 1% with respect to the total amount of the composition.

The amine derivatives (1) and compositions for external application to the skin have excellent effects in retarding aging of the skin, particularly in normalizing ekeratinization and in preventing and improving pigmentation of the skin, and in addition, have remarkable effects in relieving skin problems caused by dyskeratosis and related diseases such as a cure as well as in the treatment of comedo.

EXAMPLES

The present invention will be described in more detail by way of examples, which should not be construed as limiting the invention.

Synthetic Example 1:

Synthesis of 1-(2-hydroxyethylamino)-3-(10-methylhexadecyloxy)-2-propanol [=Compound (1-1), $R^2$=H, and n=9 in formula (1)]:

(1) Synthesis of 9-bromo-1-(2-tetrahydro-pyranyloxy) nonane [=Compound (1-1a), n=9 in formula (6)]:

In a 500 ml round bottomed flask equipped with a 20 ml dropping funnel, 9-bromo-1-nonanol (21.0 g, 94.1 mmol), p-toluenesulfonic acid-$H_2O$ (0.18 g, 0.95 mmol), and chloroform (100 ml) were placed. The content of the flask was stirred while cooling on ice, and at the same time, 3,4-dihydro-2H-pyran (9.50 g, 0.11 mol) was added dropwise over 30 minutes. After stirring for further 3 hours, aqueous sodium bicarbonate solution was added. Extraction was performed using chloroform. The resulting organic layer was dried over anhydrous magnesium sulfate, filtered, and condensed under reduced pressure. The resulting residue was purified by silica gel flush chromatography. 27.8 g of the title compound was obtained as a colorless oil (yield: 96%).

$^1$H-NMR($CDCl_3$, ppm) :1.10–2.05(m, 20H), 3.22–3.58 (m, 4H), 3.64–3.96 (m, 2H), 4.50–4.62 (m, 1H).

(2) Synthesis of 10-methyl-1-(2-tetrahydropyranyloxy)-10-hexadecanol [=Compound (1-1b), m=5 and n=9 in formula (8)]:

In a 50 ml two-necked flask equipped with a 10 ml dropping funnel and a reflux condenser, magnesium (135 mg, 5.55 mmol) and anhydrous tetrahydrofuran (1 ml) were placed. The content of the flask was stirred in a nitrogen atmosphere. While occasionally heating the flask with a dryer, 9-bromo-1-(2-tetrahydropyranyloxy)nonane (1.47 g, 5.05 mmol) in anhydrous tetrahydrofuran (8 ml) was added dropwise over 20 minutes. After stirring for further 40 minutes at room temperature, 2-octanone (0.87 ml, 5.5 mmol) was added dropwise over 10 minutes, followed by a further 1 hour stirring. Subsequently, the temperature was elevated to 60° C. and stirring was effected for 1 hour. Aqueous ammonium chloride solution (10 ml) was added and extracted with diethylether. The resulting organic layer was washed with water, dried over anhydrous sodium sulfate, filtered, and condensed under reduced pressure. The resulting residue was purified by silica gel flush chromatography. 1.47 g of the title compound was obtained as a colorless oil (yield: 82%).

$^1$H-NMR($CDCl_3$, ppm): 0.88 (t,3H, J=6.6 Hz), 1.10–1.95 (m, 20H). 3.30–3.60 (m, 2H), 3.65–3.98 (m, 2H), 4.52–4.64 (m, 1H).

(3) Synthesis of 10-methyl-1-hexadecanol [=Compound (1-1c), and n=9 in formula (3)]:

In a 200 ml round bottomed flask equipped with a reflux condenser, 10-methyl-1-(2-tetrahydropyranyloxy)-10-hexadecanol (1.47 g, 4.14 mmol), a 50% solution of sulfuric acid (5 ml) in water, and tetrahydrofuran (50 ml) were placed. The content of the flask was heated and stirred for 10 hours while refluxing. A 50% solution of methanol (40 ml) in water was added, and the resulting mixture was stirred for 1 hour at 60° C. Methanol was distilled off under reduced pressure. Extraction was performed with diethylether. The resulting organic layer was washed with an aqueous saturated sodium bicarbonate solution and then with water. The washed material was dried over anhydrous sodium sulfate, filtered, and condensed under reduced pressure. The resulting residue was placed in a 100 ml autoclave together with platinum oxide (0.1 g), acetic acid (1 ml), and methanol (30 ml). The mixture was stirred for 11 hours at 60° C. under a hydrogen pressure of 120 kg/cm$^2$. Subsequently, the pressure was reduced to an atmospheric level. The mixture was filtered and condensed under reduced pressure. The resulting residue was purified by silica gel flush chromatography. 447 mg of the title compound was obtained as a colorless oil (yield: 42%).

$^1$H-NMR(CDCl$_3$-D$_2$O, ppm): 0.78–0.95 (m, 6H), 0.98–1.80 (m, 27H), 3.64 (t, 2H, J=6.6 Hz).

IR(NaCl, cm$^{-1}$): 3332, 2932, 2860, 1468, 1380, 1054.

(4) Synthesis of 10-methylhexadecylglycidyl ether [=Compound (1-1d), and n=9 in formula (2)]:

In a 10 ml round bottomed flask equipped with a reflux tube, 10-methyl-1-hexadecanol (108 mg, 0.42 mmol), tetra-n-butylammonium bromide (4 ml, 0.012 mmol), epichlorohydrin (68 μl, 0.87 mmol), and n-hexane (1 ml) were placed. While stirring the content of the flask, the temperature was elevated to 45° C. in a nitrogen atmosphere. Sodium hydroxide (30 ml) was added and stirred for 3 hours under the same conditions. Water (1 ml) was added. Extraction was performed three times with n-hexane (1 ml). The extract was dried over anhydrous sodium sulfate, filtered, and condensed under reduced pressure. The resulting residue was purified by silica gel flush chromatography. 112 mg of the title compound was obtained as a colorless oil (yield: 85%).

$^1$H-NMR(CDCl$_3$ppm): 0.77–0.95 (m,6H), 0.99–1.69 (m, 27H), 2.61 (dd, 1H, J=2.7, 5.0 Hz), 2.80 (dd, 1H, J=4.3, 5.0 Hz). 3.10–3.20 (m, 1H), 3.31–3.58 (m, 3H), 3.71 (dd, 1H, J=3.1, 11.5 Hz).

IR(NaCl, cm$^-$): 2928, 2860, 1466, 1114.

(5) Synthesis of 1-(2-hydroxyethylamino)-3-(10-methylhexadecyloxy)-2-propanol (1-1):

By use of ethanol (4 ml), 10-methylhexadecylglycidyl ether (100 mg, 0.32 mmol) was transferred to a 10 ml dropping funnel, which was fitted to a 20 ml round bottomed flask containing ethanolamine (1 ml) and ethanol (0.2 ml). The content of the flask was stirred at 80° C. in a nitrogen atmosphere. The ethanol solution was added dropwise over 10 minutes. The mixture was stirred for a further 1 hour, and then condensed under reduced pressure. The resulting residue was purified by silica gel flush chromatography. 94 mg of the title compound was obtained as a pale yellow Vaseline-like material (yield: 79%).

$^1$H-NMR(CDCl$_3$, ppm): 0.75–0.98 (m,6H), 1.00–1.80 (m, 27H), 2.48–2.84 (m, 4H), 2.95–3.52 (m, 7H), 3.60–3.74 (m, 2H), 3.82–4.00 (m, 1H).

IR(NaCl, cm$^{-1}$): 3404, 2928, 2860, 1464, 1116, 1056.

Synthetic Example 2:

Synthesis of 1-(2-hydroxyethylamino)-3-(11-methylhexadecyloxy)-2-propanol [=Compound (1-2), R$^2$=H, and n=10 in formula (1)]:

The procedure of Synthetic Example 1 was repeated except that 10-bromo-1-decanol and 2-heptane were used in place of 9-bromo-1-nonanol and 2-octanone, respectively. The title compound was obtained as a pale yellow oil.

$^1$H-NMR(CDCl$_3$, ppm): 0.76–0.95 (m, 6H), 0.98–1.68 (m, 27H), 2.37–2.87 (m, 7H). 3.30–3.57 (m,4H), 3.60–3.77 (m, 2H), 3.80–4.00 (m, 1H).

IR(NaCl, cm$^{-1}$): 3400, 2932, 2860, 1466, 1380, 1116.

The NMR and IR data obtained for the following two intermediates, 11-methylhexadecanol [=Compound (1-2c), and n=10 in formula (3)]and 11-methylhexadecylglycidyl ether [=Compound (1-2d), and n=10 in formula (2)]were as follows.

(colorless oil)

¹H-NMR(CDCl₃, ppm): 0.76–0.95 (m, 6H), 1.00–1.72 (m, 28H), 3.56–3.72 (m, 2H).
IR(NaCl, cm⁻¹): 3356, 2928, 2860, 1466, 1058.

(colorless oil)

¹H-NMR(CDCl₃, ppm): 0.76–0.96(m,6H), 1.00–1.70 (m, 27H), 2.61 (dd, 1H, J=2.7, 5.0 Hz), 2.79 (dd, 1H, J=4.3, 5.0 Hz), 3.07–3.20 (m, 1H), 3.30–3.55 (m, 3H), 3.70 (dd, 1H, J=3.1, 11.5 Hz).
IR(NaCl, cm⁻¹): 2928, 2860, 1462, 1110.

Synthetic Example 3:

Synthesis of 1-(2-hydroxyethylamino)-3-(12-methylhexadecyloxy)-2-propanol [=Compound (1-3),

R²=H, and n=11 in formula (1)]:

¹H-NMR(CDCl₃, ppm): 0.77–0.94 (m,6H), 1.00–1.69 (m,27H), 2.56–2.81 (m, 4H), 3.18 (brs, 3H), 3.30–3.51 (m, 4H), 3.60–3.72 (m, 2H), 3.82–4.00 (m, 1H).
¹³C-NMR(CDCl₃, ppm): 14.2, 19.8, 23.1, 26.1, 27.1, 29.4–30.1, 32.8, 36.8, 37.1, 51.4, 52.0, 61.1, 69.2, 71.8, 73.5.
IR(NaCl, cm⁻¹): 3320, 2928, 2860, 1468, 1118, 1058.

The NMR and IR data obtained for the following two intermediates, 12-methylhexadecanol [=Compound (1-3c), and n=11 in formula (3)] and 12-methylhexadecylglycidyl ether [=Compound (1-3d), and n=11 in formula (2)] are as follows.

(colorless oil)

The procedure of Synthetic Example 1 was repeated except that 11-bromo-1-undecanol and 2-hexanone were used in place of 9-bromo-1-nonanol and 2-octanone, respectively. The title compound was obtained as a pale yellow oil.

¹H-NMR(CDCl₃, ppm): 0.77–0.96 (m, 6H), 0.98–1.70 (m, 28H), 3.57–3.70 (m, 2H).

IR(NaCl, cm⁻¹): 3340, 2928, 2860, 1468, 1056.

(1-3d)

(colorless oil)

¹H-NMR(CDCl₃, ppm): 0.77–0.95 (m,6H), 0.99–1.69(m, 27H), 2.61 (dd, 1H, J=2.7, 5.0 Hz), 2.79 (dd, 1H, J=4.3, 5.0 Hz), 3.08–3.20 (m, 1H), 3.31–3.55 (m, 3H), 3.70 (dd, 1H, J=3.1, 11.5 Hz).

IR(NaCl, cm⁻¹): 2928, 2860, 1462, 1110.

Synthetic Example 4:

Synthesis of 1-(2-hydroxyethylamino)-3-(9-cyclohexylnonyloxy)-2-propanol [=Compound (1-4), R²=H, and n=9 in formula (1)]:

(1-4)

The procedure of Synthetic Example 1 was repeated except that cyclohexanone was used in place of 2-octanone. The title compound was obtained as a colorless solid (m.p.: 48.4–49.1).

¹H-NMR(CDCl₃, ppm): 0.70–1.78 (m, 27H), 2.57–2.86 (m, 4H), 3.15 (brs, 3H), 3.30–3.52 (m, 4H), 3.60–3.75 (m, 2H), 3.84–4.00 (m, 1H).

IR(KBr, cm⁻¹): 3452, 2924, 2856, 1452, 1382, 1330, 1356, 1118, 1052, 954, 868.

The NMR and IR data obtained for the following two intermediates, 9-cyclohexyl-1-nonanol [=Compound (1-4c), and n=9 in formula (3)] and 9-cyclohexylnonylglycidyl ether [=Compound (1-4d), and n=9 in formula (2)] were as follows.

(1-4c)

(colorless oil)

¹H-NMR(CDCl₃, ppm): 0.70–1.80 (m, 28H), 3.64 (dt, 2H, J=6.5, 6.5 Hz).

¹³C-NMR(CDCl₃, ppm): 25.8, 26.5, 26.6, 26.7, 29.5, 29.6, 30.0, 32.9, 33.5, 37.6, 37.7, 63.1.

IR(NaCl, cm⁻¹): 3352, 2920, 2856, 1450, 1050.

(1-4d)

(colorless oil)

¹H-NMR(CDCl₃, ppm): 0.72–1.77 (m, 27H), 2.61 (dd, 1H, J=2.7, 5.0 Hz), 2.80 (dd, 1H, J=4.3, 5.0 Hz), 3.10–3.20 (m, 1H), 3.31–3.57 (m, 3H), 3.70(dd, 1H, J=3.1, 11.5 Hz).

IR(NaCl, cm⁻¹): 2928, 2856, 1454, 1112.

Synthetic Example 5:

Synthesis of 1-(2-hydroxyethylamino)-3-(10-cyclohexyldecyloxy)-2-propanol [=Compound (1-5), R²=H, and n=10 in formula (1)]:

(1-5)

The procedure of Synthetic Example 1 was repeated except that 10-bromo-1-decanol and cyclohexanone were used in place of 9-bromo-1-nonanol and 2-octanone, respectively. The title compound was obtained as a colorless solid.

¹H-NMR(CDCl₃, ppm): 0.70–1.78 (m, 29H), 2.60–2.86 (m,4H), 3.02 (brs, 3H), 3.31–3.51 (m, 4H), 3.62–3.74 (m, 2H), 3.83–4.00 (m, 1H).

IR(KBr, cm⁻¹): 3424, 2924, 2856, 1454, 1120, 1092, 1050.

The NMR and IR data obtained for the following two intermediates, 10-cyclohexyl-1-decanol [=Compound (1-5c), n=10 in formula (3)] and 10-cyclohexyldecylglycidyl ether [=Compound (1-5d), and n=10 in formula (2)] were as follows.

(1-5c)

(colorless oil)

¹H-NMR(CDCl₃, ppm): 0.72–1.85 (m, 30H), 3.64 (t, 2H, J=6.4Hz),

IR(NaCl, cm⁻¹): 3332, 2932, 2856, 1452, 1054.

(1-5d)

(colorless oil)

¹H-NMR(CDCl₃, ppm): 0.72–1.77 (m, 29H), 2.61 (dd, 1H, J=2.7, 5.0 Hz), 2.80 (dd, 1H, J=4.3, 5.0 Hz), 3.10–3.20 (m, 1H), 3.31–3.57 (m, 3H), 3.70 (dd, 1H, J=3.1, 11.5 Hz).

IR(NaCl, cm⁻¹): 2928, 2856, 1452, 1110.

Synthetic Example 6:

Synthesis of 1-(2-hydroxyethylamino)-3-(11-cyclohexylundecyloxy)-2-propanol [=Compound (1-6), (1-5)

R²=H, n=11 in formula (1)]:

(1-6)

The procedure of Synthetic Example 1 was repeated except that 11-bromo-1-undecanol and cyclohexanone were used in place of 9-bromo-1-nonanol and 2-octanone, respectively. The title compound was obtained as a colorless solid.

¹H-NMR(CDCl₃, ppm): 0.71–1.78(m, 31H), 2.60–2.88 (m,4H), 3.11(brs,3H), 3.32–3.52 (m, 4H), 3.61–3.76 (m, 2H), 3.84–4.00 (m, 1H).

¹³C-NMR(CDCl₃, ppm): 26.1–26.5, 29.5–30.0, 33.5, 37.6, 37.7, 51.3, 51.9, 60.9, 69.1, 71.8, 73.4.

IR(KBr, cm⁻¹): 3448, 2928, 2856, 1470, 1456, 1100, 1060.

The NMR and IR data obtained for the following two intermediates, 11-cyclohexyl-1-undecanol [=Compound (1-6c), and n=11 in formula (3)] and 10-cyclohexyldecylglycidyl ether [-Compound (1-6), and n=11 in formula (2)] were as follows.

(1-6c)

(colorless oil)

¹H-NMR(CDCl₃, ppm): 0.70–1.85 (m, 32H), 3.54–3.70 (m, 2H).

¹³C-NMR (CDCl₃, ppm): 25.7, 26.4, 26.7, 26.8, 29.3, 29.5–29.6, 29.9, 32.7, 33.4, 37.5, 37.6, 63.0.

IR(NaCl, cm⁻¹): 3336, 2924, 2856, 1452, 1056.

(1-6d)

(colorless oil)

¹H-NMR(CDCl₃, ppm): 0.72–1.77 (m, 31H); 2.61 (dd, 1H, J=2.7, 5.0 Hz), 2.80 (dd, 1H, J=4.3, 5.0 Hz), 3.10–3.20 (m, 1H), 3.31–3.57 (m, 3H), 3.70 (dd, 1H, J=3.1, 11.5 Hz).

¹³C-NMR(CDCl₃, ppm): 26.1, 26.5, 26.8, 26.9, 29.5–30.0, 33.5, 37.6, 37.7, 44.3, 50.9, 71.5, 71.8.

IR(NaCl, cm⁻¹): 2928, 2856, 1450, 1106.

Synthetic Example 7:

Synthesis of 1-(2-hydroxyethylamino)-3-(11-cyclopentylundecyloxy)-2-propanol [=Compound (1-7), R²=H, and n=11 in formula (1)]:

(1-7)

The procedure of Synthetic Example 1 was repeated except that 11-bromo-1-undecanol and cyclopentanone were used in place of 9-bromo-1-nonanol and 2-octanone, respectively. The title compound was obtained as a colorless solid (m.p. 59.0–60.0).

¹H-NMR(CDCl₃, ppm): 0.70–1.82 (m, 29H), 2.60–2.85 (m,4H), 2.95 (brs,3H), 3.32–3.41 (m,4H), 3.62–3.72 (m,2H), 3.84–3.98 (m, 1H).

¹³C-NMR(CDCl₃, ppm): 25.2, 26.1, 28.8, 29.5–30.0, 32.8, 36.3, 40.2, 51.3, 51.9, 61.0, 69.1, 71.8, 73.4.

IR(KBr, cm⁻¹): 3452, 2924, 2856, 1472, 1120, 1092, 1054.

The NMR and IR data obtained for the following two intermediates, 11-cyclopentyl-1-undecanol [=Compound (1-7c), and n=11 in formula (3)] and 11-cyclopentylundecylglycidyl ether [=Compound (1-7d), and n=11 in formula (2)] were as follows.

(1-7c)

$^1$H-NMR(CDCl$_3$, ppm): 0.91–1.81 (m, 30H), 3.64 (dt, 2H, J=6.1, 6.4 Hz).
IR(NaCl, cm$^{-1}$): 3336, 2928, 2860, 1468, 1058.

(colorless solid) (1-7d)

$^1$H-NMR(CDCl$_3$, ppm): 0.74–1.82 (m,29H), 2.61 (dd, 1H, J=2.7, 5.0 Hz), 2.80 (dd, 1H, J=4.1, 5.0 Hz), 3.10–3.20 (m, 1H), 3.31–3.57 (m, 3H), 3.70 (dd, 1H, J=3.1, 11.4 Hz).
IR(NaCl, cm$^{-1}$): 2928, 2860, 1468, 1108.

Synthetic Example 8:

Synthesis of 1-(2-hydroxyethylamino)-3-(11-cycloheptylundecyloxy)-2-propanol [=Compound (1-8), R$^2$=H, and n=11 in formula (1)]:

(1-8)

The procedure of Synthetic Example 1 was repeated except that 11-bromo-1-undecanol and cycloheptanone were used in place of 9-bromo-1-nonanol and 2-octanone, respectively. The title compound was obtained as a colorless solid (m.p. 49.5–50.4).

$^1$H-NMR(CDCl$_3$, ppm): 1.00–1.77 (m, 33H), 2.59–2.84 (m, 4H), 2.99 (brs,8H), 3.30–3.50 (m, 4H), 3.60–3.73 (m, 2H), 3.82–3.98 (m, 1H).

$^{13}$C-NMR(CDCl$_3$, ppm): 26.1, 26.6, 27.5, 28.6, 29.5–29.7, 30.0, 34.7, 38.3, 39.3, 51.3, 51.9, 61.0, 69.1, 71.8, 73.4.

IR(KBr, cm$^{-1}$): 3424, 2924, 2856, 1460, 1120, 1094, 1052.

The NMR and IR data obtained for the following two intermediates, 11-cycloheptyl-1-undecanol [=Compound (1-8c), and n=11 in formula (3)] and 11-cycloheptylundecylglycidyl ether [=Compound (1-8d), and n=11 in formula (2)] were as follows.

(1-8c)

$^1$H-NMR(CDCl$_3$, ppm): 1.02–1.77 (m, 34H), 3.65 (dt, 2H, J=6.3, 6.5 Hz).
IR(NaCl, cm$^{-1}$): 3336, 2928, 2856, 1464, 1056.

(1-8d)

$^1$H-NMR(CDCl$_3$, ppm): 1.20–1.77 (m, 33H), 2.61 (dd, 1H, J=2.7, 5.0 Hz), 2.80 (dd, 1H, J=4.2, 5.0 Hz), 3.10–3.20 (m,1H), 3.31–3.56(m,3H), 3.70 (dd, 1H, J=3.1, 11.4 Hz).
IR(NaCl, cm$^{-1}$): 2928, 2856, 1464, 1108.

Synthetic Example 9:

Synthesis of 1-[bis(2-hydroxyethyl)amino]-3-(12-methylhexadecyloxy)-2-propanol [=Compound (1-9), and n=11 in formula (1)]:

(1-9)

In a 10 ml round bottomed flask, 12-methylhexadecylglycidylether (100 mg, 0.32 mmol), diethanolamine (35 mg, 0.33 mmol), and ethanol (1 ml) were placed. The content of the flask was stirred for 1 hour at 80° C. in a nitrogen atmosphere. The mixture was condensed under reduced pressure, and the resulting residue was purified by silica gel flush chromatography. As a result, 88 mg of the title compound was obtained as a pale yellow oil (yield: 66%).

$^1$H-NMR (CDCl$_3$, ppm): 0.75–1.00 (m,6H), 1.02–1.80 (m, 27H), 2.30–2.90 (m, 6H), 3.30–4.00 (m, 9H), 4.90 (brs, 3H).

IR (NaCl, cm$^{-1}$): 3360, 2924, 2860, 1464, 1118, 1058.

Synthetic Example 10:

Synthesis of 1[N-methyl-2-hydroxyethylamino]-3-(12-methylhexadecyloxy)-2-propanol(1-23) [Compound(1-10), $R^2=CH_3$ and n=11 in formula(1)]

The procedure of Synthetic Example 9 was repeated except that 2-(Methylamino)ethanol was used in place of diethanolamine. The title compound was obtained as a colorless oil.

$^1$H-NMR(CDCl$_3$, ppm):
0.74–0.92 (m, 6H), 0.96–1.67 (m, 27H), 2.31 (s, 3H), 2.34–2.72 (m, 4H), 3.08 (brs, 2H), 3.29–3.50 (m, 4H), 3.55–3.66(m, 2H), 3.80–3.95(m, 1H).

IR(NaCl, cm$^{-1}$):
3392, 2932, 2860, 1464,, 1118,, 1084, 1036

Test Example 1:

Effects of amine derivatives on transglutaminase activity of epidermal keratinizing cells:

(1) Determination of transglutaminase activity:

The cells used were proliferated keratinizing cells cultured in a 10 cm Petri dish. The medium in each well was removed by suction. To each well, 2 ml of K-GM which did not contain a hypophysis extract was added to replace the medium. Subsequently, amine derivatives (1-1) to (1-9) were added. When 24 hours have elapsed, each well was washed with PBS(−) three times, and cells were exfoliated and recovered with a rubber policeman. The resulting cell suspension was centrifugally separated at 2,500 rpm×10 min. The pellet recovered was combined with 200 μl of a buffer (a) [10 mM Tris-HCl buffer, 10 mM DTT, 0.5 mM EDTA; pH 7.4], and sonicated (1 min.×2). The resulting suspension was subjected to a centrifugal separation at 25,000 rpm×30 min to obtain a supernatant. The supernatant in aliquots was dispensed to each well, and the well was combined with a reaction liquid [a solution containing 30 mM Tris-HCl buffer (pH 8.1), 60 mM CaCl$_2$ 100 μl, 30 mM DTT 100 μl, 540 μg of dimethylcasein in 100 μl distilled water, 12 mM putrescine 50 μl, 2.5 μCurie [$^{14}$C] putrescine 50 μl, and distilled water 100 μl], and incubated at 37° C. for 1 hour. Subsequently, 10% trichloroacetic acid (600 μl) was added, and the mixture was allowed to stand for 30 minutes. Using a 0.45 μm nitrocellulose membrane, the pellet was recovered. The membrane was washed with 5% ice-cold trichloroacetic acid (15 ml) containing 1% putrescine. Thereafter, radioactivity on the membrane was counted with a liquid scintillation counter.

Figure 1:
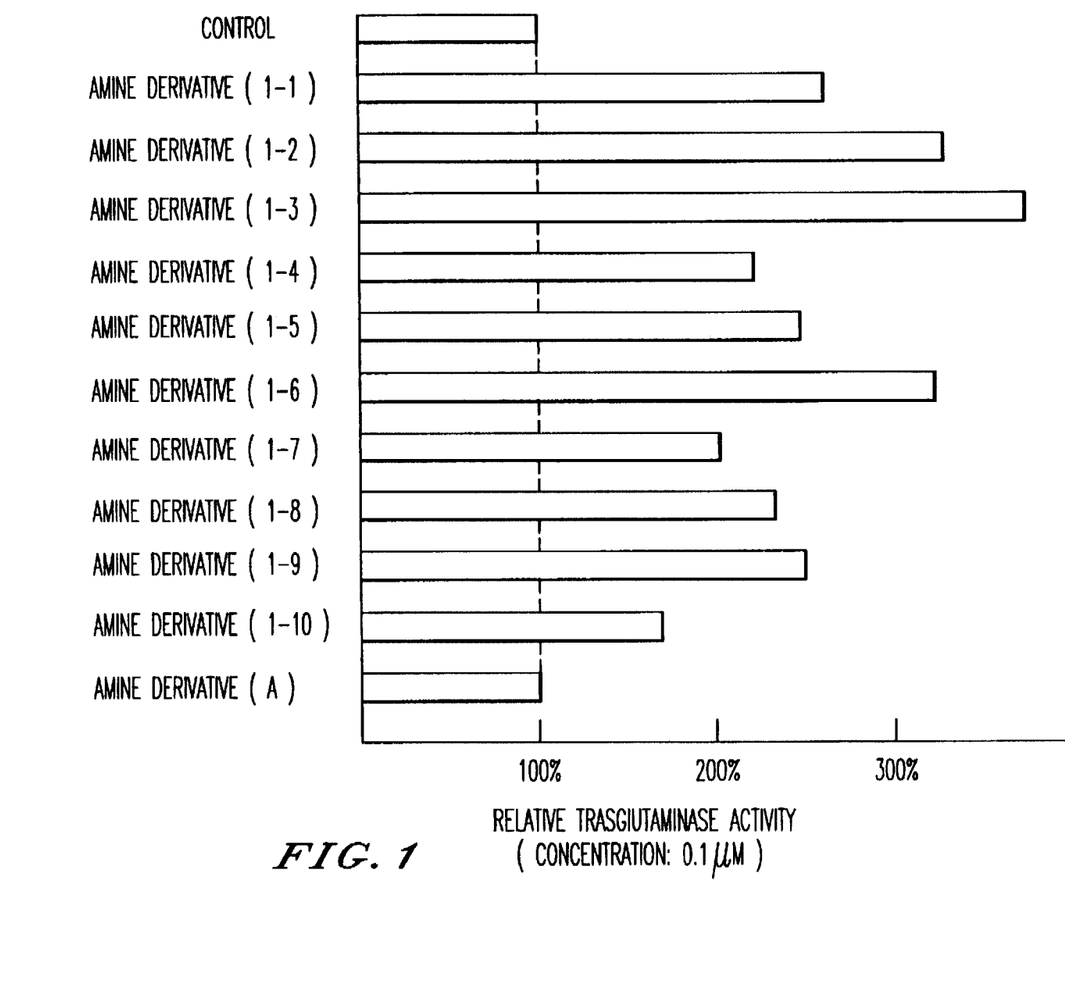
FIG. 1 is a bar graph showing the tansglutaminase activity in epidermal keratinizing cells measured when the amine derivative (1) of the present invention was added.

(2) Results:

The results are shown in FIG. 1. FIG. 1 shows the ratio of transglutaminase activity with respect to control (=100%) in cases where amine derivatives (1-1) to (1-9) each in amounts of 0.1 μM were added.

As is apparent from FIG. 1, amine derivatives (1-1) to (1-9) of the present invention increased transglutaminase activity to about 2 to 3 times that of control at a very low concentration of 0.1 μM.

In FIG. 1, amine derivative (A) is a compound disclosed in Japanese Patent Application Laid-open (kokal) No. 5-194185. This publication describes that amine derivative (A) increases transglutaminase activity to about twice the activity attained by control when the derivative (A) is used at a concentration of about 10 μM. However, amine derivative (A) did not exhibit satisfactory activity at a concentration as low as 0.1 μM.

Thus, the compounds of the present invention have transglutaminase activity 100 times greater than the activity of the compound disclosed in Japanese Patent Application Laid-open (kokai) No. 5-194185.

Test Example 2:

Effect of amine derivatives on suppressing acanthosis:

(1) Method:

The ears of 25 white guinea pigs (4–6 weeks old) were shaved. UV rays were irradiated to the shaved ears (UV-B: 1-2 MED). Immediately after irradiation, ethanol solutions each containing 0.005% amine derivative (1-3), 0.005% amine derivative (1-6), or 0.005% amine derivative (A) were separately applied to the UV-irradiated ears. The solutions were applied to the ears once a day for one week. When 1 week had elapsed, the ears of the animals were cut off to prepared sections of a skin tissue. Each tissue sample was photographed under a microscope, and the thickness of epidermis and dermis was determined. Thus, the effect achieved by each sample on acanthosis caused by UV-B irradiation was evaluated.

Figure 2:
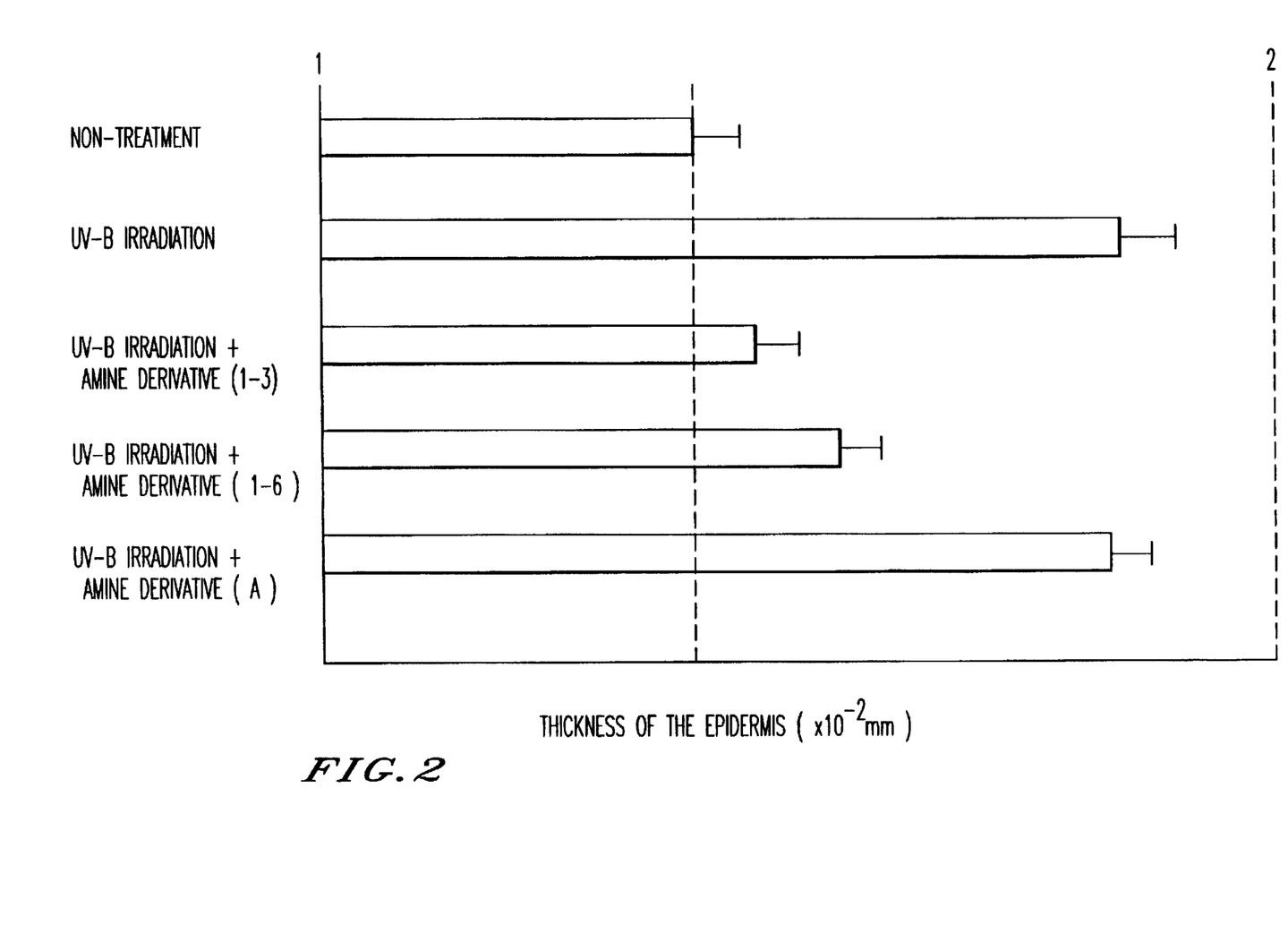
FIG. 2 is a bar graph showing action of the amine derivative (1) of the present invention in suppressing acanthosis induced by a UV irradiation.

(2) Results:

The results are shown in FIG. 2. FIG. 2 includes the results of measurement obtained in cases of UV-B irradiation only, UV-B irradiation+amine derivative (1-3), UV-B irradiation+amine derivative (1-6), and UV-B irradiation+amine derivative (A). The concentration of each sample was 0.005%.

As is apparent from FIG. 2, amine derivatives (1-3) and (1-6) effectively and meaningfully suppressed acanthosis at a very low concentration of 0.005%.

By contrast, the amine derivative (A) described in Japanese Patent Application Laid-open (kokai) No. 5-194185 did not exhibit satisfactory effect at such a low concentration.

Test Example 3:

Effect of amine derivatives on blanching UV-B pigmental spots in the back of brown guinea pigs:

The back hair of 20 brown guinea pigs was shaved carefully with hair clippers and a shaver. UV-B rays were irradiated to the shaved area in a dose three times the minimal erythema dose (MED) once a day for three days. Thus, pigmental spots were formed over a period of three weeks. Thereafter, the samples were applied twice a day every day for 1 month, and the amount of the pigmental spots which had disappeared was investigated.

A color difference meter (CMS-1200, manufactured by Murakami Shikisai) was used for the measurement. From the Munsell values obtained, L$^*$ values were calculated. Evaluation was made on the value ΔΔL$^*$ obtained by subtracting ΔL$^*$ (change over time) in the portion to which sample was not applied (solvent only, =control) from ΔL$^*$ (change over time) in the portion to which sample was applied. ΔΔL$^*$ is expressed by the following equation.

$$\Delta\Delta L^* = (L^*_1 - L^*_0) - (L'^*_1 - L'^*_0)$$

wherein

L$'^*_0$: Munsell value in the sample application portion measured before the sample was applied, L$^*_0$: Munsell value in the no sample application portion measured before the sample was applied, L$'^*_1$: Munsell value in the sample application portion measured after the sample was continuously applied over 1 month, and L$^*_1$: Munsell value in the no sample application portion measured after the sample was continuously applied over 1 month.

The evaluation was made using average $\Delta\Delta L^*$ values of 20 test animals according to the 5-rank point system shown in Table 1 below.

TABLE 1

| Points | Evaluation standard |
|---|---|
| | Improvement of pigmental spots after 1 month |
| 5 | $2.0 <\!\!/\!\!= \Delta\Delta L^*$ |
| 4 | $1.0 <\!\!/\!\!= \Delta\Delta L^* < 2.0$ |
| 3 | $0.5 <\!\!/\!\!= \Delta\Delta L^* < 1.0$ |
| 2 | $0 <\!\!/\!\!= \Delta\Delta L^* < 0.5$ |
| 1 | $\Delta\Delta L^* < 0$ |

TABLE 2

| Samples | Concentration (%) | Solvent | Evaluation point |
|---|---|---|---|
| Amine derivative (1-3) | 0.01 | 80% Ethanol | 4.25 |
| Amine derivative (1-6) | 0.01 | 80% Ethanol | 4.05 |
| Amine derivative (A) | 0.01 | 80% Ethanol | 1.50 |
| Control | — | 80% Ethanol | 1.30 |

As is apparent from Table 2, the amine derivatives (1-3) and (1-6) of the present invention effectively and meaningfully improved pigmentation in the skin at a very low concentration of 0.01%.

By contrast, amine derivative (A) described in Japanese Patent Application Laid-open (kokai) No. 6-271450 did not exhibit satisfactory effect at such a low concentration.

Test Example 4:

Effect of amine derivatives on experimental comedo formation induced by tetradecane:

(1) Method:

The inner skin of New Zealand white rabbits (male, body weight: 2.0–2.5 kg) was used. 0.3 ml each of the following sample solutions was applied to the skin once a day every day for 2 weeks: 50% tetradecane (in squalane), 0.001% amine derivative (1-3) in 50% tetradecane, 0.001% amine derivative (1-6) in 50% tetradecane, and 0.001% amine derivative (A) in 50% tetradecane. When two weeks were elapsed, the area of comedos experimentally formed in hair pouches was determined using a microscope, thereby checking the effect of the amine derivatives on the experimental comedo formation.

Figure 3:
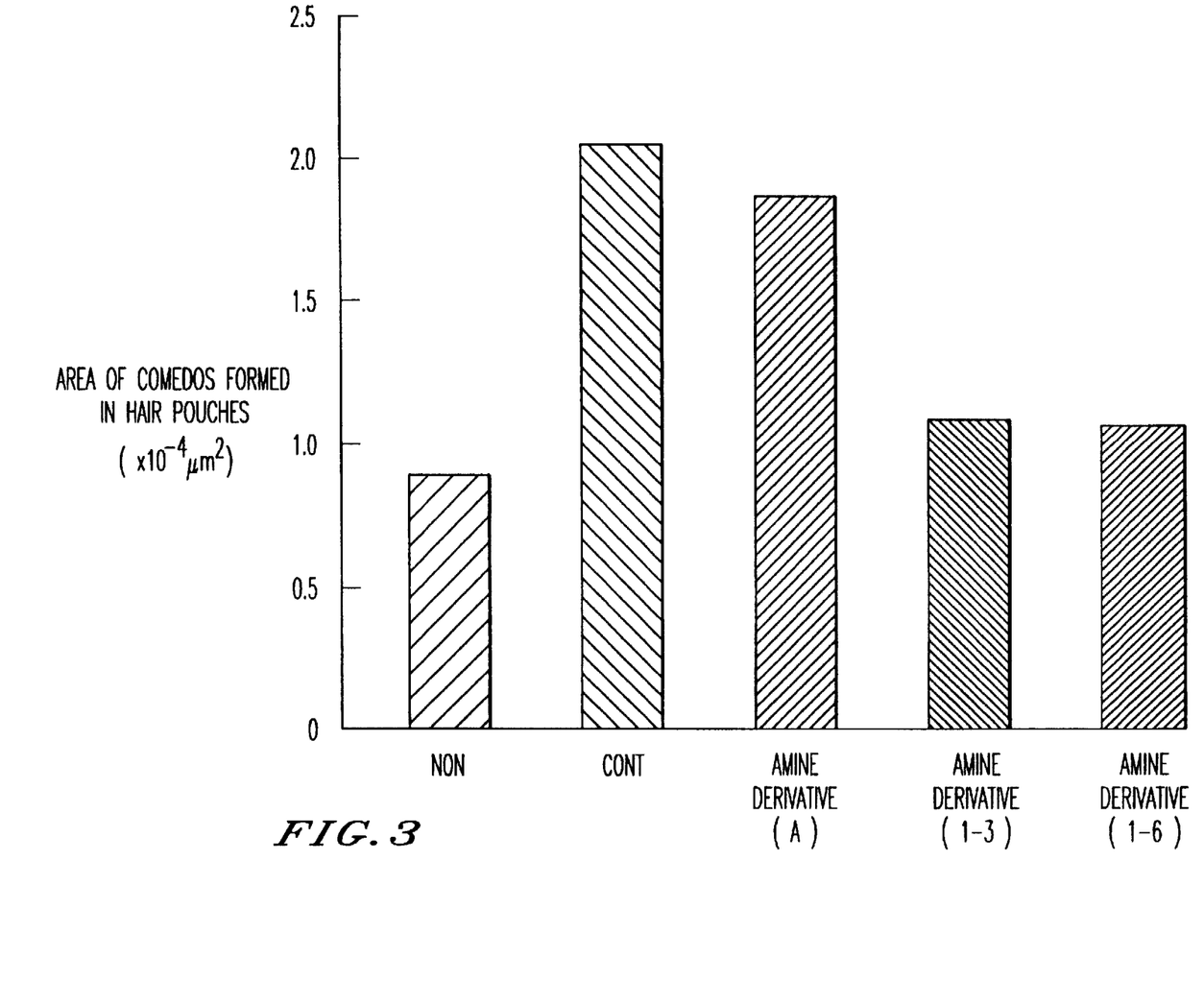
FIG. 3 is a bar graph showing action of the amine derivative (1) of the present invention in a comedo forming experiment.

(2) Results:

The results are shown in FIG. 3. FIG. 3 shows the size of experimentally formed comedos when each of tetradecane (control), tetradecane/amine derivative (1-3), tetradecane/amine derivative (1-6), and tetradecane/amine derivative (A) was used. The concentration of each sample was 0.001%.

As is apparent from FIG. 3, amine derivatives (1-3) and (1-6) effectively and meaningfully suppressed the experimentally-induced formation of comedos at a very low concentration.

By contrast, the amine derivative (A) described in Japanese Patent Application Laid-open (kokai) No. 5-194185 did not exhibit satisfactory effect at such a low concentration.

Cream:

| | (% by weight) |
|---|---|
| (1) Decaglyceryl stearate | 1.8 |
| (2) Polyoxyethylene cetyl ether | 1.2 |
| (3) Squalane | 12.0 |
| (4) Cetanol | 6.0 |
| (5) Cetyl parmitate | 3.0 |
| (6) 1,3-Butylene glycol | 6.0 |
| (7) Amine derivative (1-3) | 0.2 |
| (8) Glycerol | 3.0 |
| (9) Purified water | balance |
| (10) Preservative | suitable amount |
| (11) Perfume | trace |

Process:

Oil-phase components (1) to (7) were stirred at 80° C. While stirring, aqueous components (8) to (10) which had been heated to 80° C. in advance were added, and the mixture was emulsified. Thereafter, component (11) was added, and the mixture was cooled to room temperature with stirring to obtain a cream.

Formulation Example 2:

Milky Lotion:

| | (% by weight) |
|---|---|
| (1) Polyoxyethylene sorbitan stearate | 1.0 |
| (2) Glycerol oleate | 1.0 |
| (3) Glycerol monostearate | 0.5 |
| (4) Squalane | 6.0 |
| (5) Glyceryl trioctanoate | 2.0 |
| (6) Cetyl octanoate | 2.0 |
| (7) Stearyl alcohol | 2.0 |
| (8) Amine derivative (1-6) | 0.2 |
| (9) 1,3-Butylene glycol | 5.0 |
| (10) Glycerol | 3.0 |
| (11) Purified water | balance |
| (12) Preservative | suitable amount |
| (13) Perfume | trace |

Process:

Oil-phase components (1) to (8) were stirred at 80° C. While stirring, aqueous components (9) to (12) which had been heated to 80° C in advance were added, and the mixture was emulsified. Thereafter, component (13) was added, and the mixture was cooled to room temperature with stirring to obtain a milky lotion.

Formulation Example 3:

Lotion:

| | (% by weight) |
|---|---|
| (1) 1,3-Butylene glycol | 8.0 |
| (2) Glycerol | 4.0 |
| (3) Sodium hyarulonate | 0.1 |
| (4) Ethanol | 3.0 |
| (5) Polyoxyethylene polyoxypropylene decyl tetradecyl ether | 0.3 |
| (6) Amine derivative (1-3) | 0.05 |
| (7) Purified water | balance |
| (8) Preservative | suitable amount |
| (9) Perfume | trace |

Process:

Components (1) to (3) were stirred and dispersed. 60% in amounts of purified water was added to the dispersion (the resulting mixture is called A). Separately, components (4), (5), (6), (8), and (9) were dissolved with stirring. The remainder purified water was added thereto (the resulting mixture is called B). B was added to A with stirring. The mixture was further stirred to obtain a lotion.

Formulation Example 4:

| Beauty Lotion: | (% by weight) |
|---|---|
| (1) 1,3-Butylene glycol | 8.0 |
| (2) Glycerol | 4.0 |
| (3) Xanthan gum | 0.3 |
| (4) Sodium chondroitin sulfate | 0.1 |
| (5) Sodium hyarulonate | 0.05 |
| (6) Ethanol | 3.0 |
| (7) Polyoxyethylene polyoxypropylene decyl tetradecyl ether | 0.3 |
| (8) Amine derivative (1–6) | 0.05 |
| (9) Purified water | balance |
| (10) Preservative | suitable amount |
| (11) Perfume | trace |

Process:

Components (1) to (5) were stirred and dispersed. 65% in amounts of purified water was added to the dispersion (the resulting mixture is called A). Separately, components (6), (7), (8), (10), and (11) were dissolved with stirring. The remainder purified water was added thereto (the resulting mixture is called B). B was added to A with stirring. The mixture was further stirred to obtain a beauty lotion.

The compositions for external application to the skin according to the present invention prepared in the above Formulation Examples were effective in suppressing parakeratosis and acanthosis as well as in improving pigmentation of the skin. Moreover, the compositions were effective for the treatment of acne.

Industrial Applicability:

The compositions for external application to the skin according to the present invention remarkably suppress parakeratosis, acanthosis, errors in lipid metabolism, etc. caused by UV rays or various other factors. Moreover, they function to help maintain homeostasis of the skin. Particularly, their anti-dandruff effect and skin normalizing effect after sunburn or suntan are notable. In addition, they prevent and improve spots, freckles, and pigmentation caused by sunburns and suntans. Furthermore, the compositions of the invention are effective for treating acne.

We claim:

1. An amine derivative represented by the following formula (1) or an acid addition salt thereof:

wherein $R^1$ represents a group a cyclopentyl group, cyclohexyl group, or a cycloheptyl group, $R^2$ is a hydrogen atom or C1-C3 alkyl group which may be substituted by one or more hydroxy groups, m is an integer falling in the range from 3 to 5 inclusive, and n is an integer falling in the range from 9 to 11 inclusive.

2. The amine derivative or acid addition salt according to claim 1, wherein $R^2$ is a hydrogen atom.

3. The amine derivative or acid addition salt according to claim 1, wherein $R^1$ represents a and the sum of m and n is 14.

4. A topical composition comprising at least one amine derivative as defined in the claim 1.

5. A glycidyl ether derivative represented by the following formula (2):

wherein $R^1$ represents a group a cyclopentyl group, cyclohexyl group, or a cycloheptyl group, m is an integer falling in the range from 3 to 5 inclusive, and n is an integer falling in the range from 9 to 11 inclusive.

6. A process for the manufacture of an amine, comprising the step of reacting a glycidyl ether derivative as defined in claim 5 with an amine having the following formula:

wherein $R^2$ is a hydrogen atom or a C1–C3 alkyl group which may be substituted with one or more hydroxy groups.

7. A method of treating the skin, comprising applying the amine derivative or acid addition salt thereof of claim 1 to the skin.

8. A method for treating dyskeratosis, comprising applying an effective amount of the amine derivative or acid addition salt thereof of claim 1 to the skin.

9. A method of treating comedo, comprising applying an effective amount of the amine derivative or acid addition salt thereof of claim 1 to the skin.

10. A method of treating acanthosis, comprising applying an effective amount of the amine derivative or acid addition salt thereof of claim 1 to the skin.

11. A method for improving the keratinization of the skin, comprising applying an effective amount of the amine derivative or acid addition salt thereof of claim 1 to the skin.

12. A method for improving the pigmentation of the skin, comprising applying an effective amount of the amine derivative or acid addition salt thereof of claim 1 to the skin.

* * * * *